United States Patent [19]

Holtermann

[11] Patent Number: 4,875,899
[45] Date of Patent: Oct. 24, 1989

[54] FILTER SYSTEM WITH AN INCORPORATED GAS ESCAPE OPENING, INTENDED TO BE FITTED IN ARTIFICIAL ANUS DRAINAGE BAGS DURING THEIR MANUFACTURE

[75] Inventor: Henri Holtermann, Jean De Luz, France

[73] Assignee: Laboratories Biotrol, Paris, France

[21] Appl. No.: 191,019

[22] Filed: May 6, 1988

[30] Foreign Application Priority Data

May 14, 1987 [FR] France .................................. 87 96797

[51] Int. Cl.⁴ ............................................... A61F 5/44
[52] U.S. Cl. .................................. 604/333; 55/385.4; 55/387; 502/401
[58] Field of Search .................. 55/385 R, 387, 385.4; 640/333; 502/401, 406, 185

[56] References Cited

U.S. PATENT DOCUMENTS

| 4,460,392 | 7/1984 | Poulsen et al. | 55/387 |
| 4,579,658 | 4/1986 | Maller | 210/483 |

FOREIGN PATENT DOCUMENTS

| 65788 | 5/1977 | Japan | 502/401 |
| 123391 | 10/1978 | Japan | 502/401 |

*Primary Examiner*—Bernard Nozick
*Attorney, Agent, or Firm*—Berman, Aisenberg & Platt

[57] ABSTRACT

The invention relates to a filter system with a gas space opening, intended to be fitted in artificial anus drainage bags. This filter system is composed of a flattened oblong body comprising a core sheet, for example of open-cell expanded plastic material, impregnated with an adsorbent active material and covered by a protective film leaving free the end edges of the core sheet.

12 Claims, 2 Drawing Sheets

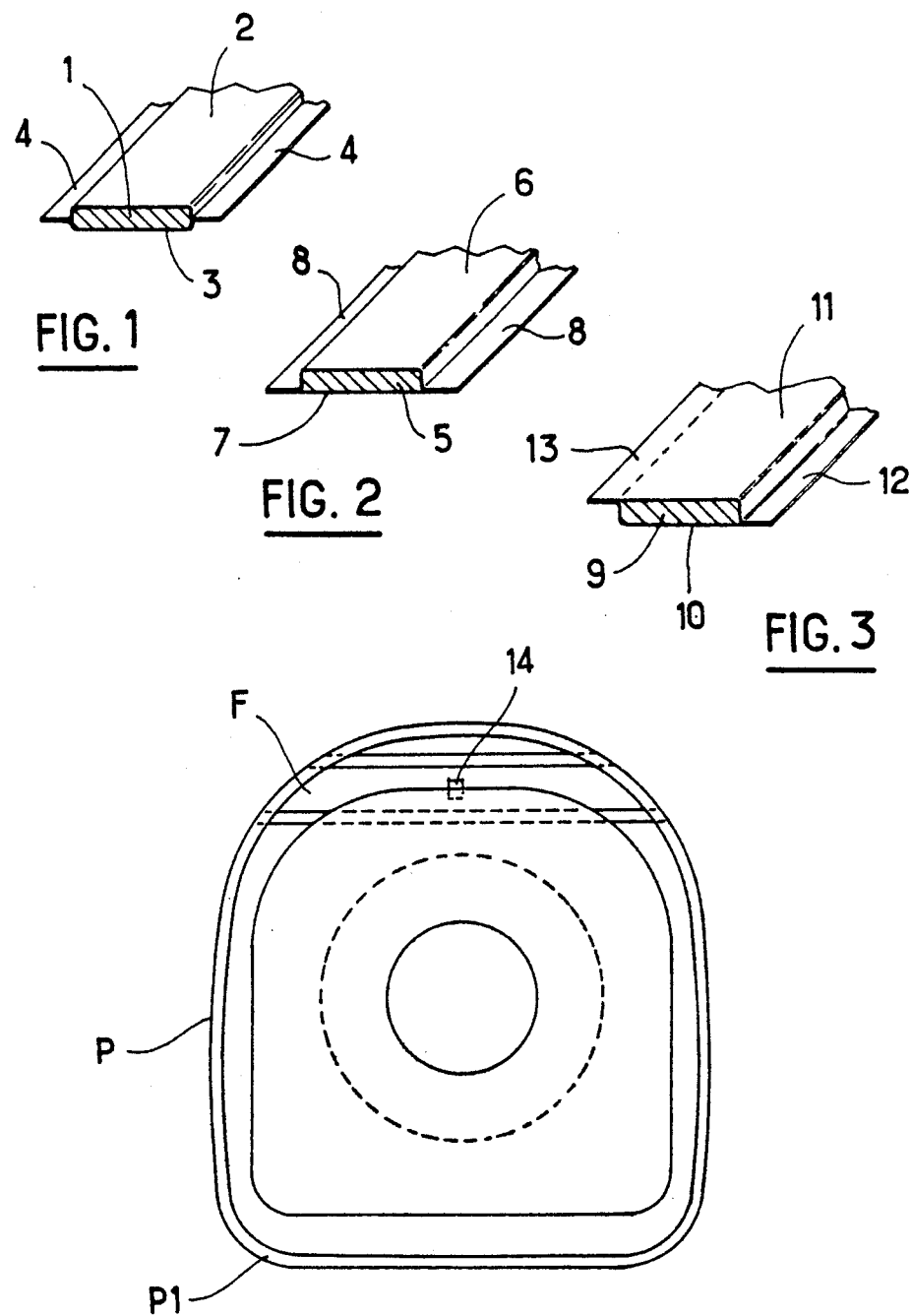

FILTER SYSTEM WITH AN INCORPORATED GAS ESCAPE OPENING, INTENDED TO BE FITTED IN ARTIFICIAL ANUS DRAINAGE BAGS DURING THEIR MANUFACTURE

The present invention relates to a new adsorbent filter for artificial anus drainage bags with a gas escape opening on the filter.

Patients who have undergone a surgical operation, for example a colostomy or an ileostomy, with creation of an artificial anus are generally equipped with collecting bags made of a pliable material, for example a plastic material, the said bags being composed of sheets or films of this material which are impermeable to gases and to odors and which are welded to each other on their periphery and of which one comprises a front opening adapted to provide a communication and a practically leakproof link between the artificial anus and the inside of the bag.

The solid or liquid excreta emitted and collected in this bag are accompanied by the emission of intestinal gases whose removal is made necessary in order to avoid an excessive inflating of the said bag. However, in the interests of the comfort of the patient and, above all, to avoid the two component films of the bag from sticking to each other in such a way as to form a narrowing prejudicial to the proper use of the bag, it is advisable to maintain inside the latter a minimum residual pressure. Moreover, given that certain intestinal gases release a foul odor which is embarrassing for the patient and those around him, it is advantageous to equip the artificial anus drainage bags with an adsorbent filter placed in the path of the gases in such a way that the latter pass through it to be purified before leaving the bag.

The filters currently used are either fixed externally or internally on one of the two component films of the bag before the production of the latter, or attached on the outer face of one of the two component films of the bag. In each of these two cases, variants have been made with the aim of obtaining more effective filters, while retaining a limited volume thereof. In some of these variants it is a question of radially deflecting the gases inside the pellet of the filter into which they have penetrated either via the periphery or via a central orifice, or else of making the gases follow a complex route via a set of diversions and obstacles inside the pellet of the filter, which has the shape of a disk or of a ring.

In practice, the filter must always remain of small thickness so as to have the least possible effect on the overall thickness of the bag. It must however have a filtering power and a capacity for adsorption of the odors sufficient to provide the wearer of a bag, equipped with such a filter, with a freedom ranging from a minimum of several hours to a period as long as 12 hours, 24 hours, and, if possible, even longer. If it is a filter incorporated in the bag at the time of its manufacture, it must at all events retain all its effectiveness for as long as the equipment remains in place. However, users are increasingly calling for bags with pre-incorporated filters. These are, above all, elderly patients who do not have the skill required to carry out themselves the fitting and use, which are often delicate, of separate filters. Whatever the type of filters currently on the market for drainage bags, they are as a general rule of an autonomy limited to a maximum of 12 hours, most often 6 hours, and even only a few hours, as regards the emissions of particularly malodorous gases. These periods of functioning may be regarded as insufficient, particularly in the case of equipment which can be emptied, since the patient is then forced to change equipment in which, however, the collecting part is still usable.

French Patent 81.11.757 of 15 Jun. 1981, in the name of the same Applicant, relates to a filter and opening system integrated in artificial anus drainage bags during the manufacture of the latter, in connection with a part of the peripheral zone of welding of the component films of the bag, thus producing a direct-passage filter whose discharge face empties to the outside of the bag and/or the inside of a downstream chamber which is an integral part of the bag, or completes it, and whose walls can be perforated to form an opening.

In its certificate of addition to the above patent, the Applicant described and claimed an improved filter and opening system for drainage bags, especially for colostomizing and ileostomizing, which represents an improvement to the system described in the abovementioned patent and which, while remaining extremely simple, can be incorporated in such bags, provides the means for adjusting the effective lifetime of the system in such a way that it corresponds at least to the anticipated period of use of the bag, and additionally allows the user himself to determine, as it suits him, the rate of discharge of gas to be given to this system when no pre-perforation has been carried out in the manufacturing.

An object of the present invention is to produce a filter system with an incorporated gas escape opening which, while retaining the qualities intrinsic to the filter systems already developed by the Applicant and analyzed hereinabove, has a particular design allowing it a better application in the artificial anus drainage bags in which it is fitted during manufacture.

The present invention thus relates to a filter system with an incorporated gas escape opening, intended to be fitted in artificial anus drainage bags during the manufacture of the latter, in connection with a part of the peripheral zone of welding of the component films of the bag, this system constituting a direct-passage filter, this filter system being additionally characterized in that it is made up of a flattened oblong body comprising a central support or core sheet made up of a nonwoven fabric or of an open-cell expanded plastic material, and impregnated with an adsorbent active material and covered by at least one protective film leaving free the end edges incorporated in the wall of the drainage bag, this filter system comprising at least one gas escape opening in the shape of a window provided in one of the longitudinal faces of the filter.

In fact, the support of the adsorbent active material can be of any material having acceptable qualities of mechanical resistance and resistance to chemical agents, for example an expanded polyurethane, an expanded polyester or an expanded polyether. The adsorbent material can be made up of any compound having the adsorption characteristics appropriate for the use, for example a metal or a metalloid, or a metallic oxide or an organometallic complex or else a mixture of metal and/or metalloid and/or metallic oxide and/or organometallic complex. It is possible to envisage advantageously using activated carbon or zinc ricinoleate.

The invention also extends to all the artificial anus drainage bags incorporating the filter system described here and in the following.

Other advantages and characteristics of the present invention will emerge from a reading of the following nonlimiting description of embodiments of a filter system with an incorporated gas escape opening, with reference to the attached drawings in which:

FIG. 1 is a partial perspective view of a filter system of the present invention, called a "carbon-containing flattened filter";

FIG. 2 is a partial view in perspective of a first embodiment variant of the filter system of the invention;

FIG. 3 is a partial perspective view of a second embodiment variant of the filter system with gas escape opening of the invention;

FIG. 4 is a plan view of a mini drainage bag equipped with a flattened carbon filter of the invention.

Figure 5:
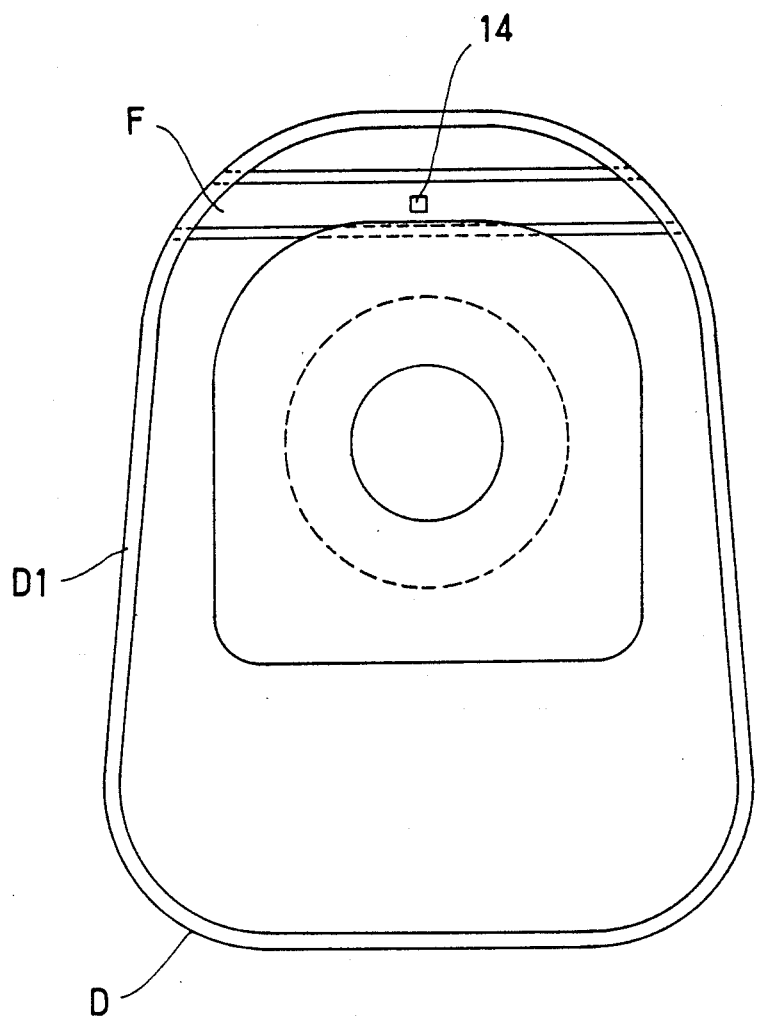
FIG. 5 is a plan view of an "integral" drainage bag equipped with a flattened carbon filter of the invention.

In the embodiment of FIG. 1, the flattened carbon filter of the invention is made up of a central support or core sheet 1 of open-cell expanded plastic material, for example polyurethane, impregnated with an adsorbent material, for example activated carbon combined with ferric oxide. This central core sheet 1 is covered by two films 2, 3 of plastic material impermeable to gases. The films 2 and 3 join essentially at the halfway point of the thickness of the core sheet 1 in such a way as to form edge zones or rims 4.

In the embodiment of FIG. 2, the flattened carbon filter of the invention is also made up of an adsorbent core sheet 5 covered by two protective films 6 and 7 which join at the level of the edges of one of the longitudinal faces of the core sheet 5 in such a way as to form rims 8.

In the embodiment of FIG. 3, the flattened carbon filter is also made up of an internal adsorbent core sheet 9 protected by two impermeable films 10 and 11 which join, on one side, at the level of a lower edge of the core sheet 9 in such a way as to form a rim 12 and, on the other side, at the level of an upper edge of the said core sheet 9 in such a way as to form an opposite rim 13.

The respective core sheets 1, 5, 9 of the flattened carbon filters of the invention are made up of a polyurethane foam impregnated with an activated carbon advantageously containing 10% of ferric oxide. The leakproof films or membranes 2, 3; 6, 7; and 10, 11 are advantageously made up of a plastic material impermeable to gases.

Among the impermeable plastics appropriate for leakproofing the filter, there may be mentioned polyvinylidene chloride, the combinations of polyvinylidene chloride and polyethylene, the combinations of polyvinylidene chloride and ethylene vinyl acetate, the combinations of polyethylene and polyethylene terephthalate, the combinations of polyethylene and polyvinyl alcohol.

FIG. 4 shows a filter F incorporated in a drainage bag P called a "mini bag", made up in the conventional manner of a transparent complex film welded peripherally to a white complex film in such a way as to form a peripheral welding zone P1. In the fitting zone of the filter F, the end zones of the latter fit in a leakproof manner inside the peripheral zone P1, in such a way as to leave the unprotected peripheral zones of the filter F open to the air. Inside the bag P, the filter F is provided with at least one gas escape opening 14 made in one of its faces.

As shown in FIG. 5, a filter F also having a gas escape opening 14 is also fitted inside a drainage bag of greater volume D manufactured in a conventional manner from a transparent film and a white film of impermeable plastic in such a way as to form a peripheral zone D1 passed through in a leakproof manner by the end zones, of the filter F, open to the air.

Thus, according to the present invention, the problem posed by the complexity of the filter systems for gas escape is solved, in particular as regards the leak-proofing and positioning of the gas escape opening in the filter, and this by virtue of the special structure of the flattened carbon filter of the present invention as defined hereinabove and claimed in the following.

It is clear that the invention is in no way limited to the embodiments described hereinabove with reference to the attached drawings, but that it embraces all the modifications and variants resulting from the same basic principle.

What we claim is:

1. A substantially flat elongated gas filter system suitable for incorporation within and as part of an artificial anus drainage bag, the gas filter system having two ends, two sides, two faces, a central permeable core sheet impregnated with adsorbent active material and surrounded by gas impermeable protective plastic material which is in direct contact with the central permeable core sheet throughout its entire length, and at least one gas escape opening in the protective plastic material on one of the faces, the two ends being free from the gas impermeable plastic material and thus comprising further gas escape openings.

2. A filter system as claimed in claim 6 wherein the central permeable core sheet is composed of open-cell expanded polyurethane.

3. A filter system as claimed in claim 1, wherein the adsorbent material is activated carbon.

4. A filter system as claimed in claim 1, wherein the adsorbent material is zinc ricinoleate.

5. A filter as claimed in claim 1 wherein the central permeable core sheet is composed of nonwoven fabric or of open-cell expanded plastic material.

6. A filter as claimed in claim 1 wherein the protective plastic material extends beyond the central permeable core sheet on both sides thereof, thus making the filter system substantially wider than the central permeable core sheet without altering its substantially flat dimension.

7. A filter system as claimed in claim 1 wherein the adsorbent material is impregnated with ferric oxide.

8. An artificial anus drainage bag comprising component plastic films sealed together along their peripheral edges, the bag containing between the component plastic films a gas filter system as claimed in claim 1, the respective ends of the filter system extending through the peripheral edges which surround and are sealed to the protective plastic material of said filter system.

9. A drainage bag as claimed in claim 8 wherein the central permeable core sheet is composed of nonwoven fabric or of open-cell expanded plastic material.

10. A drainage bag as claimed in claim 9 wherein the open-cell expanded plastic material is expanded polyurethane.

11. A drainage bag as claimed in claim 9 wherein the adsorbent material is activated carbon.

12. A drainage bag as claimed in claim 9 wherein the adsorbent material is zinc ricinoleate.

* * * * *